US012636147B2

(12) United States Patent
Tseng et al.

(10) Patent No.: US 12,636,147 B2
(45) Date of Patent: May 26, 2026

(54) TEMPORARY VASCULAR VALVE AND RELATED SYSTEMS AND METHODS

(71) Applicants: The Regents of the University of California, Oakland, CA (US); United States Government as represented by the Department of Veterans Affairs, Washington, DC (US)

(72) Inventors: Elaine Tseng, South San Francisco, CA (US); Liang Ge, Foster, CA (US); John Ashley, Danville, CA (US); Brenna Lord, San Francisco, CA (US)

(73) Assignees: The Regents of the University of California, Oakland, CA (US); United States Government as represented by the Department of Veterans Affairs, Washington, DC (US)

( * ) Notice: Subject to any disclaimer, the term of this patent is extended or adjusted under 35 U.S.C. 154(b) by 1048 days.

(21) Appl. No.: 17/527,840

(22) Filed: Nov. 16, 2021

(65) Prior Publication Data

US 2022/0151776 A1      May 19, 2022

Related U.S. Application Data

(60) Provisional application No. 63/114,029, filed on Nov. 16, 2020.

(51) Int. Cl.
*A61F 2/24*          (2006.01)

(52) U.S. Cl.
CPC .......... *A61F 2/2418* (2013.01); *A61F 2/2427* (2013.01); *A61F 2250/0059* (2013.01)

(58) Field of Classification Search
CPC .... A61F 2/2418; A61F 2/2409; A61F 2/2427; A61F 2/24; A61F 2/2433; A61F 2250/0059; A61B 17/12022; A61B 17/1204
See application file for complete search history.

(56) References Cited

U.S. PATENT DOCUMENTS

| | | | | |
|---|---|---|---|---|
| 3,671,979 A | * | 6/1972 | Moulopoulos | ........ A61F 2/2427 |
| | | | | 623/2.11 |
| 4,056,854 A | * | 11/1977 | Boretos | ................. A61F 2/2436 |
| | | | | 623/2.18 |
| 4,339,831 A | * | 7/1982 | Johnson | ................. A61F 2/2418 |
| | | | | 137/854 |
| 5,769,816 A | * | 6/1998 | Barbut | ....................... A61F 2/01 |
| | | | | 604/93.01 |

(Continued)

FOREIGN PATENT DOCUMENTS

| | | | | | |
|---|---|---|---|---|---|
| WO | | WO-9916382 A2 | * | 4/1999 | .............. A61F 2/011 |
| WO | | WO-0110342 A1 | * | 2/2001 | ........... A61F 2/0105 |
| WO | | WO-2016050751 A1 | * | 4/2016 | ........... A61F 2/9517 |

*Primary Examiner* — Seema Mathew
(74) *Attorney, Agent, or Firm* — Ballard Spahr LLP

(57) ABSTRACT

Various temporary or removable valve devices having an expandable frame comprising a flexible material and a membrane attached to the expandable frame, wherein the temporary valve device is movable into an expanded configuration for deployment of the device in a target vascular area and further is movable into a collapsed configuration for both delivery of the device to the target vascular area and for removal of the device from the target vascular area.

20 Claims, 13 Drawing Sheets

(56)　　　　　　References Cited

U.S. PATENT DOCUMENTS

| | | | | |
|---|---|---|---|---|
| 6,277,139 | B1 * | 8/2001 | Levinson ............. | A61B 17/221 |
| | | | | 606/127 |
| 6,361,545 | B1 * | 3/2002 | Macoviak ........... | A61B 17/221 |
| | | | | 606/151 |
| 6,635,070 | B2 * | 10/2003 | Leeflang ................ | A61B 17/22 |
| | | | | 606/200 |
| 2005/0119688 | A1 * | 6/2005 | Bergheim ............... | A61F 2/013 |
| | | | | 606/200 |
| 2007/0100420 | A1 * | 5/2007 | Kavanagh ......... | A61B 17/1204 |
| | | | | 623/1.11 |
| 2010/0036474 | A1 * | 2/2010 | Bergheim ............. | A61F 2/2476 |
| | | | | 623/1.11 |
| 2010/0217385 | A1 * | 8/2010 | Thompson ............ | A61F 2/2418 |
| | | | | 623/2.1 |
| 2012/0226340 | A1 * | 9/2012 | Leschinsky ............. | A61F 2/958 |
| | | | | 623/2.11 |
| 2014/0039544 | A1 * | 2/2014 | Bergheim ............. | A61F 2/2476 |
| | | | | 606/200 |
| 2014/0200658 | A1 * | 7/2014 | Ho ..................... | A61B 17/1204 |
| | | | | 623/2.11 |
| 2020/0069421 | A1 * | 3/2020 | Pasquino ................ | A61F 2/011 |
| 2024/0225354 | A1 * | 7/2024 | Vansickel ........... | A47J 37/0704 |

* cited by examiner

TEMPORARY VASCULAR VALVE AND RELATED SYSTEMS AND METHODS

CROSS-REFERENCE TO RELATED APPLICATION(S)

This application claims the benefit under 35 U.S.C. § 119(e) to U.S. Provisional Application 63/114,029, filed Nov. 16, 2020 and entitled "Temporary Vascular Valve and Related Systems and Methods," which is hereby incorporated herein by reference in its entirety.

FIELD

The various embodiments herein relate to cardiac valve repair and/or replacement methods and devices, and more specifically to temporary replacement valve devices and related methods.

BACKGROUND

Various valvular conditions can cause serious issues for patients prior to transcatheter or surgical repair or replacement with a permanent valve implant. In endocarditis, acute valvular insufficiency can result in flash pulmonary edema for left-sided valvular lesions, or hepatic congestion and failure for right-sided valvular lesions, and potentially hemodynamic instability. Similarly, known clinical procedures such as transcatheter aortic valve replacement ("TAVR") and percutaneous aortic balloon valvuloplasty ("PABV") can also result in complications during the procedures. More specifically, in PABV for native aortic stenosis or bioprosthetic valve stenosis, acute aortic insufficiency after the PABV may not be tolerated hemodynamically and require stabilization of the patient for either TAVR or surgical aortic valve replacement ("SAVR"). Further, in TAVR, if the transcatheter aortic valve is deployed too low with severe aortic insufficiency ("AI") and hemodynamic collapse, support of the patient can be required while the second TAVR is prepped.

Other situations that can require patient support include either degenerated TAVR or SAVR. Since TAVR has thinner leaflets, and higher leaflet stresses than SAVR, engineering estimates suggest that TAVR has a durability of 8 years compared to SAVR with clinically-shown durability of up to 20 years. For patients who desire a completely percutaneous valve replacement either after TAVR or SAVR degeneration, support for the patient during removal of the degenerated TAVR or balloon valvuloplasty or bioprosthetic valve fracture of SAVR is essential. Removal of the degenerated TAVR if within a native valve, another TAVR or SAVR, or removal of degenerated TAVR or SAVR leaflets, will result in wide open aortic insufficiency and hemodynamic collapse.

Known replacement valves are permanent devices that are implanted via standard procedures (open heart procedures, for example) or percutaneous procedures. Certain known percutaneously-delivered permanent devices have large, complex expandable frame structures that are used to expand and maintain the expansion of the valve devices. Other known permanent, non-percutaneous devices are rigid (non-expandable) devices that have fabric disposed around the perimeter such that the devices can be sewn into place via the fabric.

There is a need in the art for a temporary valve device and/or percutaneous method of implantation to support a patient with temporary valve support prior to transcatheter surgical repair or replacement with a permanent valve implant.

BRIEF SUMMARY

Discussed herein are various temporary valve devices and methods of implanting such devices.

In Example 1, a temporary valve device comprises an expandable frame comprising a flexible material and a membrane attached to the expandable frame, wherein the temporary valve device is movable into an expanded configuration for deployment of the device in a target vascular area, and wherein the temporary valve device is movable into a collapsed configuration for both delivery of the device to the target vascular area and for removal of the device from the target vascular area.

Example 2 relates to the temporary valve device according to Example 1, wherein the temporary valve device further comprises at least one support strut attached to the expandable frame.

Example 3 relates to the temporary valve device according to Example 1, wherein the expandable frame and the membrane have a substantially circular, conical, or umbrella-like shape in the expanded configuration.

Example 4 relates to the temporary valve device according to Example 1, wherein the expandable frame and the membrane have a substantially circular shape in the expanded configuration.

Example 5 relates to the temporary valve device according to Example 1, wherein a portion of the membrane comprises a flap, wherein at least a portion of the flap is not attached to the expandable frame, wherein the flap is movable between a closed position and an open position in which an opening is defined between the flap and the expandable frame.

Example 6 relates to the temporary valve device according to Example 5, wherein the flap is substantially flexible or substantially rigid during use.

Example 7 relates to the temporary valve device according to Example 1, wherein the expandable frame is tensioned with an axially outward force when the device is in the collapsed configuration, wherein the axially outward force is sufficient to retain the device within the target vascular area when the frame is expanded to the expanded configuration.

Example 8 relates to the temporary valve device according to Example 7, wherein the axially outward force can be overcome by an external force to urge the device back into the collapsed configuration for removal of the device from the target vascular area.

Example 9 relates to the temporary valve device according to Example 1, further comprising a flexible skirt attached to an outer circumference of the expandable frame.

Example 10 relates to the temporary valve device according to Example 1, wherein the device is positionable within the target vascular area such that the device allows flow of fluid in one direction but inhibits flow of the fluid in an opposite direction.

Example 11 relates to the temporary valve device according to Example 1, wherein the temporary valve device in the collapsed configuration is positionable within a lumen of a delivery device.

Example 12 relates to the temporary valve device according to Example 11, wherein the delivery device comprises a delivery sheath or a delivery catheter.

In Example 13, a removable valve device comprises an expandable frame, at least one support strut attached to the expandable frame, and a flexible membrane attached to the expandable frame and at least one of the at least one support struts, wherein the removable valve device is movable between a collapsed configuration and an expanded configuration, and wherein the removable valve device is removable in the collapsed configuration after use.

Example 14 relates to the removable valve device according to Example 13, wherein the support strut is attached at a first end to the expandable frame and at a second end to a guidewire.

Example 15 relates to the removable valve device according to Example 13, wherein the device is positionable within a target vascular area such that the device allows flow of fluid in one direction but inhibits flow of the fluid in an opposite direction.

Example 16 relates to the removable valve device according to Example 13, wherein the expandable frame is tensioned with an axially outward force when the device is in the collapsed configuration, wherein the axially outward force is sufficient to retain the device within a target vascular area when the frame is expanded to the expanded configuration, wherein the axially outward force can be overcome by an external force to urge the device back into the collapsed configuration for removal of the device from the target vascular area.

In Example 17, a method of positioning a temporary valve device within a patient comprises inserting the temporary valve device in a collapsed configuration through a blood vessel to a target location in the patient, the temporary valve device comprising an expandable frame and a membrane attached to the expandable frame. The method further comprises expanding the temporary valve device in the blood vessel such that the expandable frame is disposed against an inner wall of the blood vessel, whereby the temporary valve device provides hemodynamic support to the patient, and collapsing the temporary valve device back to the collapsed configuration and retracting the temporary valve device through the blood vessel.

Example 18 relates to the method according to Example 17, wherein the retracting the temporary valve device further comprises retracting the temporary valve device through a delivery device disposed in the blood vessel.

Example 19 relates to the method according to Example 17, wherein the expanding the temporary valve device comprises releasing the temporary valve device from a delivery device such that an axially outward force resulting from a tensioned state of the temporary valve device in the collapsed configuration causes the temporary valve device to expand to an expanded configuration.

Example 20 relates to the method according to Example 17, wherein the collapsing the temporary valve device comprises applying an external force to overcome the axially outward force and thereby urge the temporary valve device into the collapsed configuration.

While multiple embodiments are disclosed, still other embodiments will become apparent to those skilled in the art from the following detailed description, which shows and describes illustrative embodiments. As will be realized, the various implementations are capable of modifications in various obvious aspects, all without departing from the spirit and scope thereof. Accordingly, the drawings and detailed description are to be regarded as illustrative in nature and not restrictive.

DETAILED DESCRIPTION

Figure 1A:
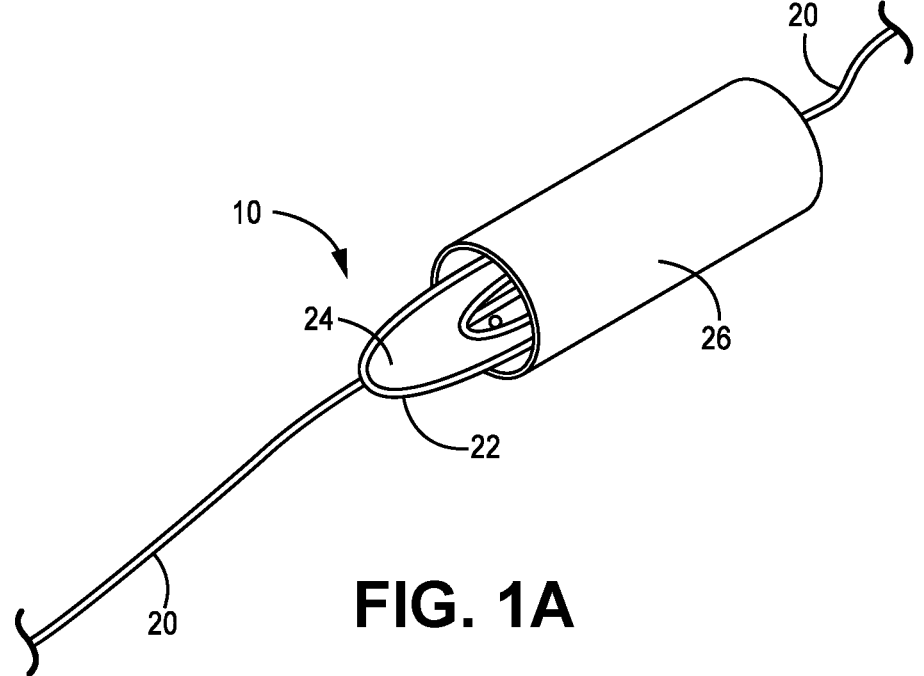
FIG. 1A is a perspective view of an embodiment of a temporary valve, according to one embodiment.

The various implementations herein relate to a device that includes a temporary valve which can be used to manage patients where acute valve insufficiency is not tolerated hemodynamically. Some embodiments relate to a percutaneously-delivered, deployable valve device. In certain exemplary situations, the embodiments can provide support until a permanent valve replacement is in place. There are various clinical scenarios where application of a temporary valve implementation as disclosed or contemplated herein can stabilize patient hemodynamics.

The term "temporary" as used herein with respect to the various valve implementations disclosed or contemplated herein relates to the amount of time that the valve device remains implanted in the patient. According to certain embodiments, the term "temporary" means a period of time ranging from about 5 minutes to about 60 days. Alternatively, the period of time ranges from about 30 minutes to about 30 days.

The term "about," as used herein, refers to variation in the numerical quantity that can occur, for example, through typical variation in device components and equipment, with respect to any quantifiable variable, including, but not limited to, size, length, radius, circumference, mass, volume, time, distance, wave length, frequency, voltage, current, electromagnetic field, etc. Further, given device manufacturing and production procedures used in the real world, there is certain inadvertent error and variation that is likely through differences in the manufacture, source, or purity of the ingredients used to make the components or carry out the methods and the like. Whether or not modified by the term "about," the claims include equivalents to any quantities set forth therein.

Various situations in which a temporary valve can be implanted include those discussed in the Background. For example, placement of a temporary valve according to any embodiment disclosed or contemplated herein can stabilize a patient with endocarditis until an operation can be undertaken or while sterilizing the valve until a transcatheter valve is placed. If the infected valve leaflets are removed percutaneously, the temporary valve can maintain valve competence. Further, in certain implementations, use of the temporary valve can be continued as antibiotics are administered to sterilize the site until definitive valve replacement is performed either surgically or by a permanent transcatheter valve option. In acute aortic insufficiency, a temporary valve embodiment can be placed through percutaneous femoral, axillary, carotid or brachial access in a Hufnagel position above the coronaries in the mid or distal ascending aorta or in the descending thoracic aorta. For severe tricuspid insufficiency, a temporary valve in accordance with any implementation herein can be deployed from the internal jugular vein, the subclavian veins, and/or femoral veins to the superior vena cava and inferior vena cava to allow recovery of liver function prior to tricuspid valve repair or replacement. For severe pulmonary insufficiency, a temporary valve in accordance with any implementation herein can also be deployed from the internal jugular vein or subclavian veins to the superior vena cava and/or femoral veins to the inferior vena cava to traverse the tricuspid valve to reach the pulmonary artery. Similarly for severe mitral insufficiency, the mitral valve for temporary valve placement could be accessed antegrade through a transseptal approach or retrograde through the aortic valve to reach the mitral valve. In other situations, patients with valvular regurgitation may develop acute or chronic heart failure which, in addition to medical treatment or an intra-aortic balloon pump, may benefit from temporary valvular competence to optimize management and normalize organ perfusion until definitive valvular therapy is performed.

Other exemplary clinical situations for placement of a temporary valve embodiment include during TAVR and PABV. In PABV, placement of a temporary valve in the ascending or descending thoracic aorta can stabilize the patient for either TAVR or SAVR. In TAVR, if the transcatheter aortic valve is deployed too low with severe AI and hemodynamic collapse, a temporary valve may support the patient while the second TAVR is prepped.

Another possible use for a temporary valve in accordance with the various implementations herein would be in the situation of a completely percutaneous treatment for degenerated TAVR and SAVR. For patients who desire a completely percutaneous valve replacement either after TAVR or SAVR degenerates, a temporary valve can be placed during removal of the degenerated TAVR or SAVR. For example, placement of a temporary valve embodiment in the Hufnagel position above the coronaries in the ascending aorta or in the descending thoracic aorta, can provide valve competence while removal of the degenerated valve and/or valve leaflets is performed and allow time for the subsequent TAVR replacement of the degenerated valve.

The various embodiments of a temporary valve which function as one-way valves to prevent leakage as described herein can also be used for hemodynamic support whenever it is needed for a specified duration when the native, TAVR, SAVR, or other heart valve is not providing sufficient support.

The various temporary valve embodiments disclosed or contemplated herein are one-way valves that allow for blood flow in solely one direction.

Figure 1B:
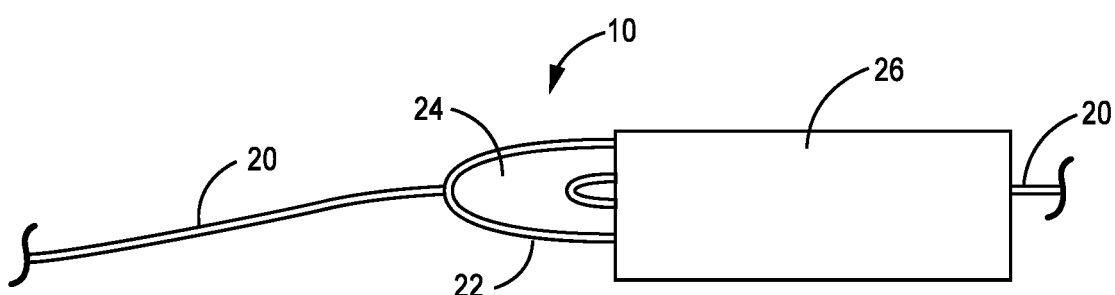
FIG. 1B is the side view of the temporary valve of FIG. 1A.

FIGS. 1A-1B show a temporary valve 10, according to one exemplary embodiment, for use in a patient's vascular system. The temporary valve 10 is comprised of a collapsible outer frame 22 and a valve membrane 24. The valve membrane 24 can be attached to the collapsible outer frame 22 by any number of known means, including, but not limited to, adhesives, ultrasonic welding, insert molding, thermal bonding, or one or more fasteners. The fasteners can include, but are not limited to, clips, staples, rivets, sutures, screws and the like. The temporary valve 10 can be collapsed into a small diameter to fit inside a delivery sheath 26. The temporary valve 10 can be configured to be advanced over a guide wire 20 or it can be affixed to the guide wire 20 and advanced along with the guide wire 20. By collapsing the temporary valve 10 into a delivery sheath 26 and advancing it over or with a guide wire 20, the temporary valve can be easily inserted into a patient's vasculature and advanced to a desired location where it can be expanded for use. The temporary valve 10 in FIGS. 1A-1B is shown partially extended from the delivery sheath 26 such that a portion of the valve 10 is disposed within the sheath 26 and a portion is disposed outside of the sheath 26. The temporary valve 10 can also be fully covered by the delivery sheath 26 to provide for insertion and advancement. The delivery sheath 26 in FIGS. 1A-1B is shown as a short length of cylindrical tubing. The delivery sheath 26 can also be an extended length of tubing having a length that is sufficient to cover the temporary valve 10 and the guide wire 20. Alternatively, the delivery sheath 26 can be any length varying from a length that covers solely the temporary valve 10 in its collapsed configuration up to and including a length that extends up to the entire length of the patient's vasculature such that the delivery sheath 26 extends outside the patient's vasculature, and further can have any length therebetween. As discussed above, in certain implementations, the temporary valve 10 is delivered to the target location within the patient via the vasculature using the delivery sheath 26. The delivery sheath 26 can be any one of a number of known, commercially-available catheter sheaths such as the Telescope™ guide extension catheter or Launcher™ guide catheter from Medtronic®, the CONVEY™ Guiding Catheter or GUIDEZILLA™ II Guide Extension Catheter from Boston Scientific®, known coronary guide catheters, any other known catheter sheaths, or the like.

The collapsible outer frame 22 can be one or more segments of wire made from any number of materials that can be elastically deformed to collapse such that the valve can be inserted into and moveably disposed inside the delivery sheath 26 and then expand to the desired dimensions once the delivery sheath 26 is retracted. Materials such as nickel titanium alloys, polycarbonate, high density polyethylene, acrylonitrile butadiene styrene, nitinol, and the like can be used for the collapsible outer frame 22, such that the frame 22 can move between collapsed and expanded configurations. Some of the materials (such as nitinol, for example) are shape memory materials such that the frame 22 is tensioned in its collapsed configuration such that when the force applied thereto is released, the frame 22 returns to the expanded configuration (its untensioned state).

The frame 22 can be caused to move between its collapsed and expanded configurations via any known mechanism or feature. For example, in certain embodiments, the frame 22 is constructed of one of the shape memory materials discussed above, and external force is applied to the frame 22 to urge it into its collapsed configuration for insertion and for retraction via the delivery sheath 26. Alternatively, the frame 22 has articulating joints between the sections of the frame that allow for collapse and expansion and are tensioned to urge the frame into its expanded configuration. In a further alternative, any known mechanism or feature can be incorporated into the frame 22 to allow for it to move between its collapsed and expanded configurations.

The frame 22 can be urged into its collapsed configuration for insertion into the delivery sheath 26 (for delivery) and for retraction via the delivery sheath 26 via any known mechanism or feature. For example, in certain embodiments, a removal device or mechanism can be used. The device can be a separate removal device, or one that is connected to or incorporated into the temporary valve 10. One such exemplary removal device that can be coupled to or incorporated into any temporary valve embodiment disclosed or contemplated herein is described in U.S. Published Patent Application 2021/0022894, which is incorporated herein by reference in its entirety. Alternatively, any known removal device can be used. In a further alternative, when it is time to remove the temporary valve 10, the collapsible device 10 can be removed by simply urging the delivery sheath 26 back over the device 10 (or urging the device 10 back into the sheath 26) such that the frame 22 is urged into its collapsed configuration by the walls of the sheath 26 as the frame 22 (and entire device 10) is urged into the sheath 26 (or the sheath 26 is urged over the device 10). According to yet another alternative in which the device 10 has an expandable balloon (also referred to herein as a "deflatable skirt" in some embodiments) attached to or integral with the device 10 (as discussed below with respect to certain implementations), the device 10 is urged into its collapsed configuration by deflating the balloon.

The valve membrane 24 can be made of any material that is also flexible or thin and compressible or foldable, such that it can collapse inside the delivery sheath 26, expand when the collapsible outer frame 22 expands, collapse again for retraction/removal of the device 10 (as discussed above), and is impermeable to blood. For example, the valve membrane material 24 can be, but is not limited to, pericardium, polyurethane, polycarbonate, polyester, high density polyethylene, ultrahigh molecular weight polyethylene, polytetrafluoroethylene, expanded polytetrafluoroethylene, silicone, acrylonitrile butadiene styrene, Dacron, or any other similar material having similar characteristics. These materials can be uniform sheets, or they can be configured as woven sheets or woven materials.

Figure 2A:
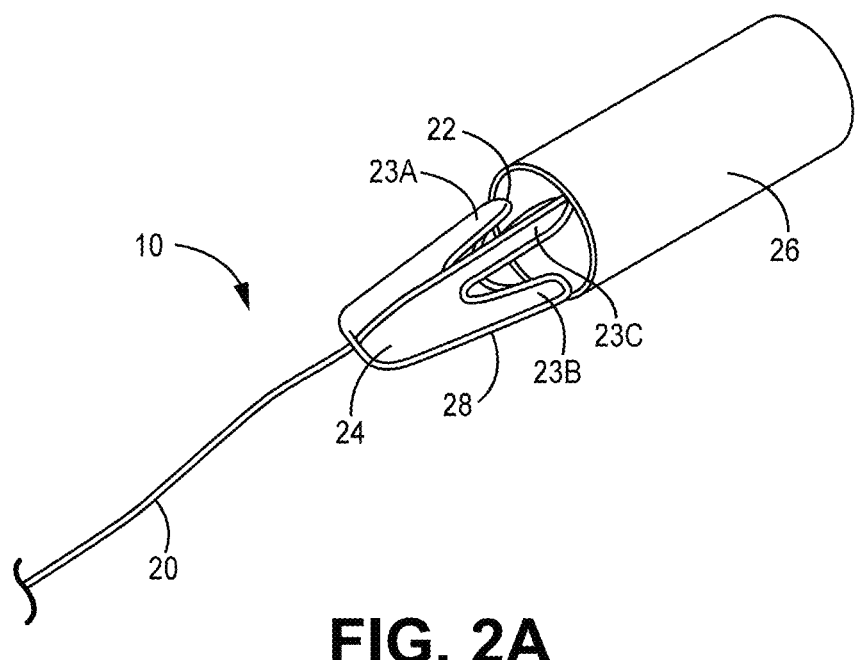
FIG. 2A is a perspective view of another embodiment of a temporary valve.
Figure 2B:
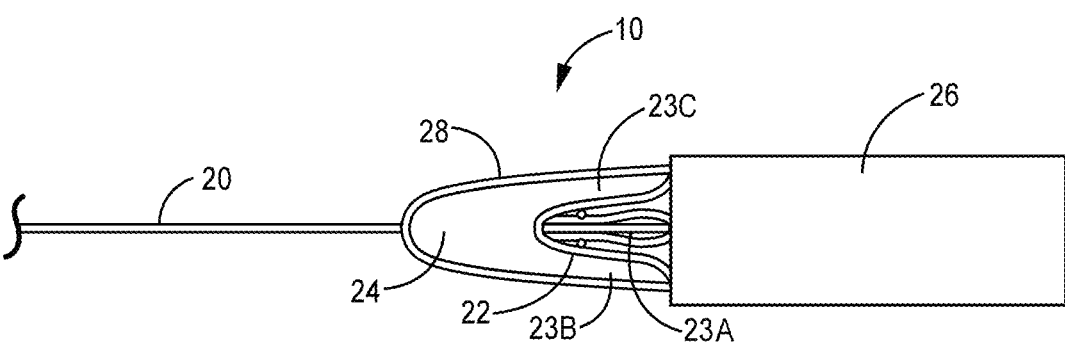
FIG. 2B is the side view of the temporary valve of FIG. 2A.

Referring now to FIGS. 2A-2B, one implementation of the temporary valve 10 is shown nearly fully advanced distally out of the delivery sheath 26. Here the collapsible outer frame 22 and valve membrane 24 can be clearly seen folded up to fit inside the delivery sheath 26. The temporary valve 10 is shown folded into three sections or lobes 23A-23C, but it is understood that it could be collapsed in any number of manners, including folded in a greater or lesser number of sections, rolled up, compressed like an accordion, or any combination of these configurations/methods.

Figure 3A:
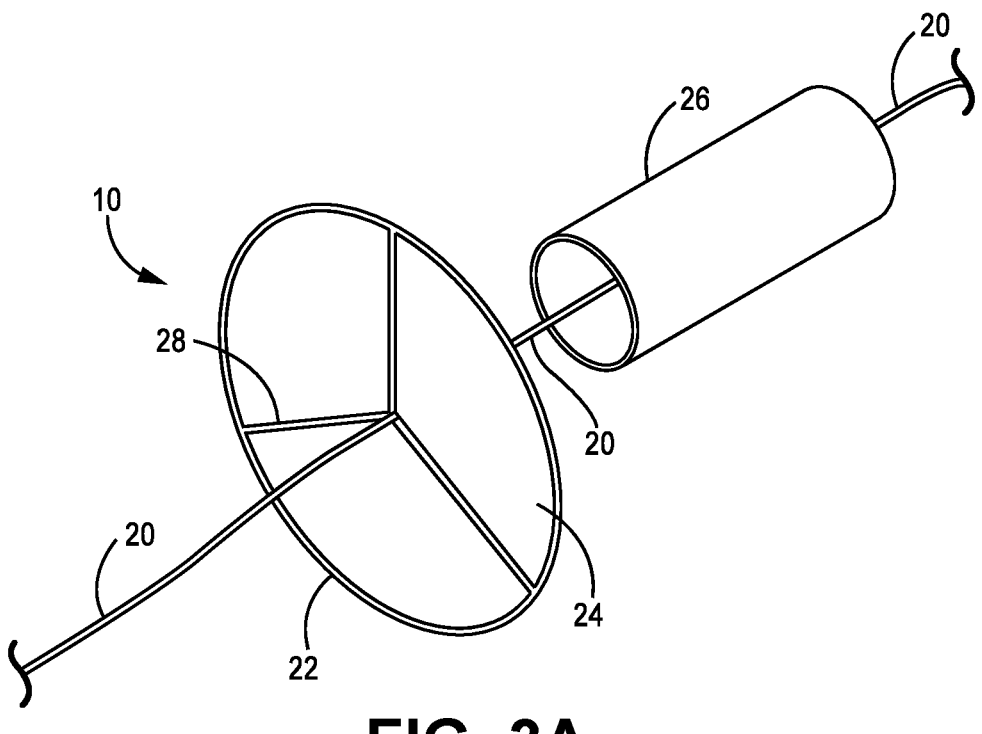
FIG. 3A is a perspective view of a further embodiment of a temporary valve.
Figure 3B:
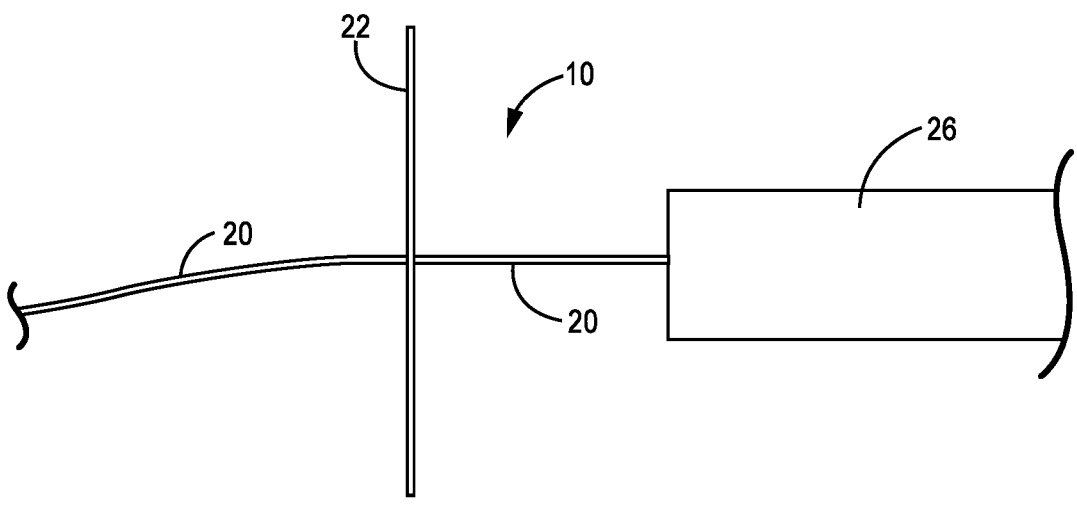
FIG. 3B is the side view of the temporary valve of FIG. 3A.

Referring to FIGS. 3A-3B, the temporary valve 10 is shown with the delivery sheath 26 completely retracted such that no portion of the valve 10 is disposed within the sheath 26. Here the collapsible outer frame 22 and valve membrane 24 are expanded into a generally circular shape with a substantially round outer diameter as shown. According to certain embodiments, this substantially round shape can be preferred as the inner diameter of the vascular system is generally circular, and in order to function as an efficient valve, the collapsible frame 22 should expand against the inner aortic wall or against the left ventricular outflow tract ("LVOT")/annulus where the native aortic valve has been removed or crushed. As aortic and annular/LVOT diameter sizes can vary from patient to patient, several versions of the device 10 can be provided in which the collapsible frame 22 can be provided in a range of diameters such that one of the several devices 10 having an appropriate/desired diameter can be selected to fit the anatomy of the patient based upon the normal physiologic sizes of the particular vascular location and ability to maintain competence. For example, in certain non-limiting examples in which any of the device 10 embodiments herein are configured for placement as a temporary aortic valve, the diameter of the device could range from about 16 to about 32 mm. Alternatively, the range can be greater for various reasons, including pediatric patients (smaller sizes) and aneurysmal aortas (larger sizes), for example. Alternatively, any known diameter for any known target vascular area is contemplated herein.

Continuing with FIGS. 3A-3B, the temporary valve 10 also has supporting struts 28. The supporting struts 28 are wire segments that can maintain connection between the collapsible outer frame 22 and valve membrane 24 on the guide wire 20. As such, in this specific embodiment, the frame 22 is a single wire disposed in a substantially circular shape, with three supporting struts that are wires coupled at one end to the frame 22 and at the other end to each other and/or the guide wire 20. While three supporting struts 28 are shown in this embodiment of the temporary valve 10, it is understood that the temporary valve 10 can be comprised of any number of supporting struts 28, not limited to, but including, 1, 2, 3, 4, 5, 6, or more. The supporting struts 28 can also provide additional support and/or expansion force for the collapsible outer frame 22 to ensure the temporary valve 10 expands against the inner wall of the aorta. The supporting struts 28 can be made of a similar flexible material as the collapsible outer frame 22 or they can be made of a more rigid supporting material where there are flexible hinges (not shown) between the supporting struts 28 and the collapsible outer frame 22 as well as flexible hinges between the supporting struts 28 and the guide wire 20. In this manner, the supporting struts 28 can efficiently hold the collapsible supporting frame 22 and valve membrane 24 in an expanded configuration relative to the guide wire 20. In an alternate embodiment, the supporting struts 28 can directly support the valve membrane 24 of the temporary valve 10 without the need for the collapsible outer frame 22. This temporary valve 10, according to certain implementations, could have an umbrella-like shape as depicted and discussed in additional detail below with respect to FIGS. 14 and 14B.

In this specific embodiment as shown in FIGS. 3A and 3B, the membrane 24 is attached to the struts 28 and the frame 22 such that there are no openings defined therebetween. In other words, there are no flaps or "leaflets" incorporated into this implementation of the device 10 as shown. Instead, the outer frame 22 is sufficiently stiff or inflexible to resist or withstand diastolic pressure and maintain its expanded configuration (as shown in both FIGS. 3A and 3B) such that the device 10 blocks blood flow back towards the heart but is not sufficiently stiff or inflexible to resist or withstand systolic blood pressure such that the frame 22 deforms or is otherwise urge toward its collapsed configuration such that the device 10 allows blood coming from the heart to flow past the outer frame 22 (between the frame 22 and the inner wall of the target valve area). Thus, the membrane 24 in this embodiment is fully attached to the frame 22 such that it is fixed around the entire outer circumference of the frame 22, and the flexibility characteristics of the outer frame 22 vis a vis the force of the blood flow provide for the control of that flow. Alternatively, the device 10 as shown in FIGS. 3A and 3B can have flaps or openings similar to those in the embodiments depicted in FIGS. 4A-4B or 5A-5B.

The collapsible, removable valve device 10 of FIGS. 3A and 3B and the other device embodiments disclosed in FIGS. 4A-14B and discussed in detail below (or contemplated herein) have certain structural advantages over known implantable artificial valve devices that allow the removable valve device 10 embodiments herein to be collapsible and removable after being positioned within the target valve area for some desired period of time. In other words, known artificial percutaneous valves are not removable and have various structural characteristics that prevent them from being removed. That is, known percutaneous artificial valves are not made to be collapsed. Instead, such known unremovable valves are made to be inserted in a collapsed state and then deployed into their expanded configurations permanently.

One advantage of all of the removable valve implementations herein is that the collapsible frame 22 is made of a sufficiently flexible material that allows for a minimal predetermined amount of force to cause the frame 22 to collapse into its collapsed configuration while having sufficient outward radial force to prevent valve incompetence under diastolic pressure when the device 10 is deployed in the target vascular area. The amount of force required to deploy and to collapse the frame 22 of this device 10 (and the various devices 10 herein) is substantially less than the force required to deploy the known artificial valves described above. More specifically, the known artificial valves are made of a rigid and/or inflexible material that is not deformable after surgical or transcatheter implantation. Hence, for known transcatheter implantation procedures, the rigid and/or inflexible material requires significant force to expand the valves into the deployed configuration, including such materials as cobalt chromium, stainless steel, and the like. As a result, such known balloon-expandable transcatheter valves require a deployment balloon that is pressurized with several times normal atmospheric pressure in order to provide sufficient force to expand the known valve device. That is, the known valves require a deployment balloon pressurized to at least 4 atmospheres and typically around 6 atmospheres. Such inflexible materials are not capable of collapsing after expansion except under the same amount of force, which cannot be delivered intravascularly. Similarly, known self-expanding transcatheter aortic valves that are not designed for transcatheter removal have self-expanding shape-memory frames with sufficient outward radial force such that they are not readily removable once implanted without surgical explantation. Thus, in contrast to the known artificial valves that preclude transcatheter removal, the various embodiments herein have flexible frames 22 made of flexible materials that allow for deploying and collapsing the device embodiments, wherein the materials require less force than known balloon-expandable and self-expanding shape-memory valves, but have sufficient outward radial force to maintain valve competence under diastolic pressure.

Given the variation in the human body, including the size of target vascular areas and varying blood pressures, etc., the range of force required to collapse any of the temporary valve devices described herein will vary depending on the required size characteristics of the patient. Thus, without being limited by specific numbers, in certain exemplary embodiments, the various devices 10 herein have flexible frames 22 made of flexible materials that allow for deploying and collapsing the device embodiments with a force that is around 0.1 to 0.66 of the amount of force required for deploying the known valves. Alternatively, the various embodiments herein have flexible frames 22 that allow for deploying and collapsing the device embodiments using a force equivalent of between about 0.33 to about 2 atmospheres. These ranges are non-limiting and exemplary in nature. The amount of force required to collapse any specific temporary valve embodiment as disclosed or contemplated herein will vary depending on the size of the device and the specific makeup of the material(s) in the flexible frame 22.

Another structural advantage of the collapsible valve embodiments herein relates to those implementations that incorporate shape memory material. More specifically, the amount of tension incorporated into the shape memory material of the various embodiments herein is less in comparison to that incorporated into the known devices that preclude transcatheter removal. In these known devices, the shape memory material must have an expansion/tensioned strength sufficient to compress the calcified native valve out of the way. As a result, the expandable components of the known devices are highly tensioned such that they expand with significant force in order to crush the calcified leaflets. In practice, as a result of this required force, the deployment of the known devices results in the inability to recollapse the device for removal once deployed. In contrast, the various device 10 implementations herein having expandable frames 22 made of one or more shape memory materials can be deployed with the ability to expand and retract the device for both insertion and removal control, accuracy, and precision, because the shape memory materials are less tensioned in comparison to the known devices and thus deploy more slowly and with less force. That is true in part because the various devices 10 herein are temporary in nature, and thus it is not critical to crush the natural leaflets or maintain a perfect fluidic seal.

Another structural advantage of the collapsible valve embodiments herein relates to those implementations that incorporate an inflatable or balloon component (as described in additional detail below). More specifically, the various device embodiments herein that have an inflatable component or balloon can remain inflated with any inflation fluid during the temporary use and thus can be deflated when its time to remove the device. In contrast, in those known devices that preclude transcatheter removal and have an inflatable balloon, such balloons are filled with an adhesive cement or hardening polymer that harden over time to permanently hold the balloon (and thus the permanent valvular device) open. Thus, the various device implementations herein with inflatable components are not filled with any type of hardening material, and instead are inflated with any known non-hardening inflation fluid.

A further advantage relates to the overall structure of the valve 10 embodiments herein. More specifically, in contrast to the known artificial valves, which typically have a substantial number of struts/supports and cells, the various valve implementations herein have a minimal number of structures. More specifically, the valve embodiments herein have a frame 22 and potentially one or more segments 28 with the membrane 24 attached thereto, with some embodiments having additional components as well, as discussed in further detail below. These various configurations having a minimal number of components facilitate the collapsibility of the embodiments.

Figure 4A:
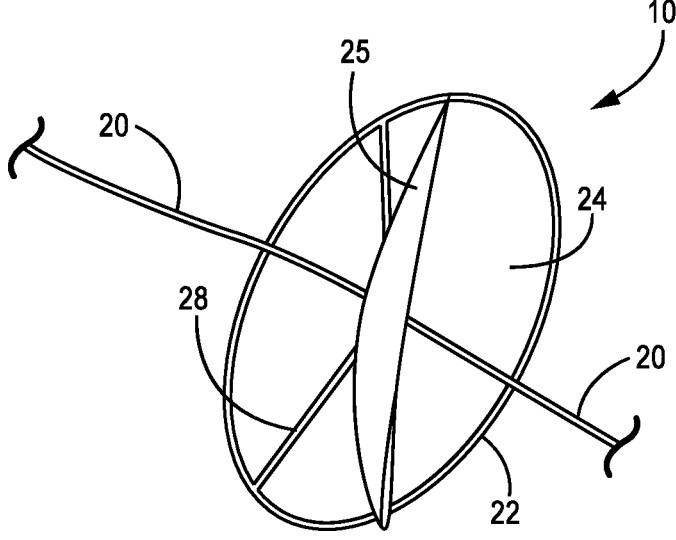
FIG. 4A is a perspective view of yet another embodiment of a temporary valve.
Figure 4B:
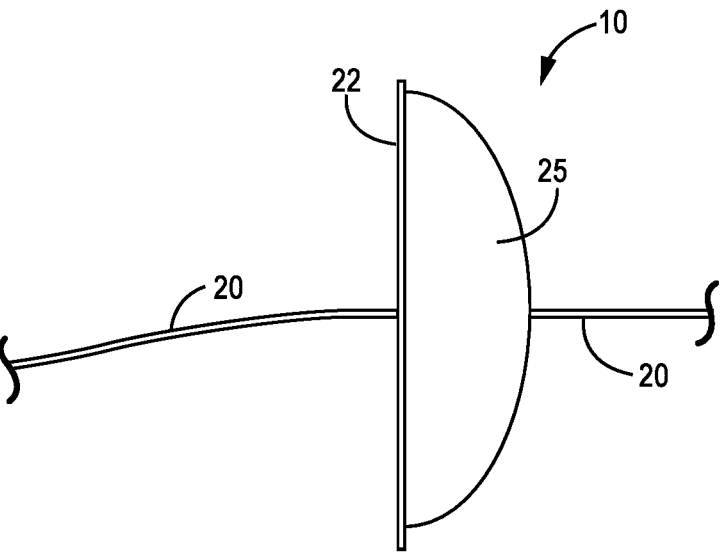
FIG. 4B is the side view of the temporary valve of FIG. 4A.

FIGS. 4A-4B depict an embodiment of the temporary valve 10 that is a flap valve 10. In this embodiment, the valve membrane 24 is attached to the collapsible frame 22 along a portion of the collapsible frame's diameter and it is not attached along another portion (thereby forming a "flap" 25). The flap 25 is moveable between a closed position in which the flap 25 is in contact with the collapsible frame 22 and an open position in which the unattached portion of the flap is disposed away from the collapsible frame 22, thereby forming an opening in the valve 10. In accordance with one exemplary implementation, the blood naturally flows from the left to the right in this figure such that the temporary valve 10 is configured to allow blood to flow downstream (away from the heart) but not upstream. Thus, when the pressure increases upstream (on the left side of the valve membrane 24 in FIGS. 4A and 4B), the flap 25 of the valve membrane 24 moves away from the collapsible frame 22 (toward it's open position) as shown to allow blood to flow in the direction of lower pressure. Thus, with reference to FIG. 4B, the higher pressure in this example is to the left of the collapsible frame 22 and the flap 25 has moved to the right of the collapsible frame 22 to form an opening as shown. According to certain embodiments, the flap 25 is urged to an open position such that the flap 25 is positioned at up to 90° in relation to collapsible frame 22. Alternatively, the flap 25 can open to a position that ranges from about 1° to about 90°, or any position in between, in relation to the frame 22. When the pressure decreases on the left side of the collapsible frame 22, the flap 25 will move back to the closed position against the collapsible frame 22, thereby creating a seal between the flap 25 and the collapsible frame 22 and preventing the blood from flowing back upstream (in this new direction of lower pressure). In this manner, the temporary valve 10 provides the function of controlling blood flow in a desired direction. In one embodiment, the movement of the flap 25 back to the closed position is caused by the change in pressure as a result of the blood flow. Alternatively, the movement of the flap 25 back to the closed position can be caused by the flap being tensioned—by shape memory material or by any known tensioning mechanism.

In certain implementations, the valve membrane 24 can be configured such that the membrane 24 has material characteristics or additional mechanisms to assist with effective operation of the membrane 24 and thus the operation of the valve 10. For example, according to some embodiments, a portion of the valve membrane 24 at or adjacent to where it attaches to the collapsible frame 22 can have increased flexibility in comparison to the rest of the membrane 24, thereby enhancing the ability of the valve membrane 24 to bend or pivot at or near the collapsible frame 22. This enhanced ability to bend or pivot allows for the temporary valve 10 to more easily open and thereby allow blood to flow past in the desired direction. Further, in some implementations, the portion of the valve membrane 24 at and/or adjacent to where the membrane 24 seals against the collapsible frame 22 can be stiffer than other portions of the membrane 24, thereby enhancing the ability of the membrane 24 to create an effective seal to prevent blood flow in the non-desired direction. In a further alternative, portions of the membrane 24 can have any known materials or characteristics that can assist with the operation thereof.

In another alternative embodiment, the valve membrane 24 can have two sections divided by a hinge portion between the two sections. In this embodiment, the membrane 24 can have a consistent stiffness across both sections and the first section can be attached to the collapsible frame 22 and the second section can be unattached, or, alternatively, both sections can be unattached. That is, the device 10 as shown in FIGS. 4A and 4B has a substantially rigid flap 25 (second section) (instead of a flexible flap 25 as discussed above) that is coupled to the device 10 or the second section via a hinge mechanism. The hinge mechanism allows the second section of outer frame and the portion of the valve membrane 24 attached to the second section to move away from the collapsible frame 22 to allow blood to flow. The hinge mechanism also allows the first section of the outer frame and the portion of the valve membrane 24 attached to the first section to maintain connection of the valve membrane 24 to the collapsible frame 22. In yet another alternate embodiment of the temporary valve 10, the second section or flap 25 of outer frame can be comprised of a magnetic material and the collapsible frame 22 that the second section seals against can also be comprised of a magnetic material. As such, the two magnetic materials can create a magnetic field that is weak enough to allow the blood pressure to separate the second section of the outer frame from the collapsible frame 22 to allow blood to flow in a desired direction but are also configured to create a magnetic field that is strong enough to seal the second portion of the outer frame against the collapsible frame 22 to prevent blood flowing in non-desired direction. In accordance with certain of the implementations having one or more flaps (such as flap 25), the one or more flaps can move into an open position such that the one or more flaps is positioned at up to 90° in relation to collapsible frame 22. Alternatively, the one or more flaps can open to a position that ranges from about 5° to about 90°, or any position in between, in relation to the frame 22.

Figure 5A:
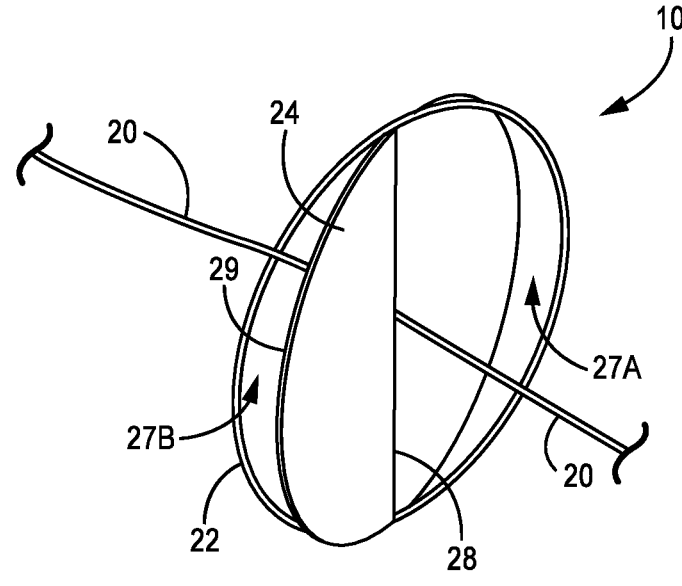
FIG. 5A is a perspective view of another implementation of a temporary valve.
Figure 5B:
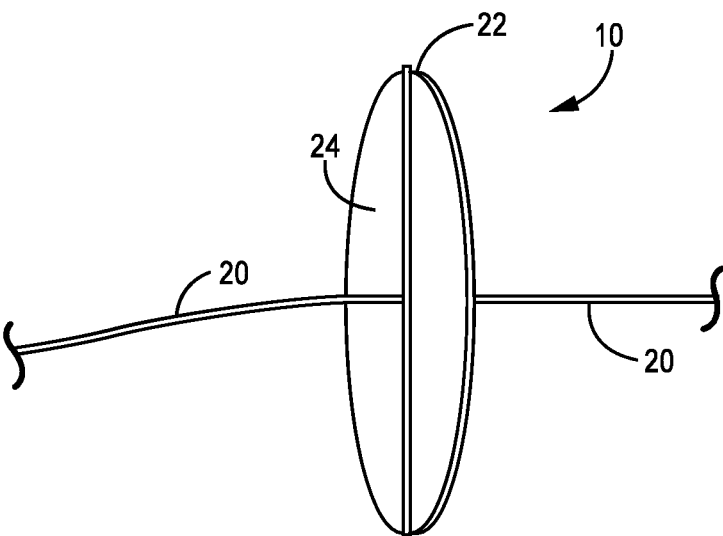
FIG. 5B is the side view of the temporary valve of FIG. 5A.

Another embodiment of the temporary valve 10 is depicted in FIGS. 5A-5B, in which the device 10 is a pivoting valve 10. In this embodiment, the valve membrane 24 is attached to a support strut 28 that form a central axis across the collapsible frame 22 as best shown in FIG. 5A. More specifically, the valve frame 22 has a circular shape, with a single strut 28 coupled at both ends to the frame 22 such that the strut 28 extends across the diameter of the frame 22 (from one side of the frame to the other). Alternatively, the strut 28 as shown could constitute two struts 28, with a first strut 28 coupled at one end to the frame 22 and at the other end to the guide wire 20 and the second strut coupled at one end to the frame 22 at a location on the frame opposite the attachment point of the first strut 28 and at the other end to the guide wire 20. Alternatively, instead of being coupled to the guide wire 20, the two struts 28 can be coupled to each other at a location near or adjacent to the guide wire 20. In this implementation, the valve membrane 24 is rotatable as a single unit around the axis established by the support strut(s) 28 in relation to the collapsible frame 22. The outer circumference of the membrane 24 can, in certain embodiments, be supported by a separate membrane frame 29 such that the membrane 24 is coupled to the membrane frame 29 and both the membrane frame 29 and membrane 24 are rotatable in relation to the frame 22. Alternatively, the membrane 24 is sufficiently rigid or inflexible to maintain its circular shape during use. When the pressure increases on one side of the valve membrane 24, the membrane 24 pivots around the support struts 28 such that two openings 27A, 27B form between the membrane 24 and the frame 22, thereby allowing blood to flow through the openings 27A, 27B in the direction of lower pressure. As shown in FIG. 5A, the higher pressure is to the left of the collapsible frame 22 and one half of the valve membrane 24 has moved to the right of the support struts 28 and collapsible frame 22. When the pressure decreases on the left side of the collapsible frame 22, the valve membrane 24 will pivot back against the collapsible frame 22, thereby closing the two openings 27A, 27B and creating a seal and preventing the blood from flowing back in the direction of lower pressure. In one embodiment, the movement of the membrane 24 back against the collapsible frame 22 is caused by the change in pressure as a result of the blood flow. Alternatively, the movement of the membrane 24 back to the closed position can be caused by the membrane 24 being tensioned—by shape memory material or by any known tensioning mechanism. The valve membrane 24 in this embodiment is configured to be stiff enough to seal against the collapsible frame 22 to prevent blood flow in the non-desired direction and also flexible enough to be collapsed into the delivery sheath 26 for placement into the desired location in the patient's vasculature. In this manner, the temporary valve 10 provides the function of controlling blood flow in a desired direction.

According to an alternative embodiment, the pivoting valve 10 can also hinge in the middle (referred to as a butterfly valve) where it is attached to the support struts 28 such that the valve membrane 24 has two sections that can rotate independently of each other at the axis established by the support struts 28. In such an embodiment, increased pressure on the left of the collapsible frame 22 causes both separate sections of the pivoting valve membrane 24 to rotate such that they move towards the right in the figure. With decreased pressure on the left of the collapsible frame 22, both sections of the pivoting valve membrane 24 rotate such that they move towards the left in the figure and seal against the collapsible frame 22. In one embodiment, the rotation of the two sections back against the collapsible frame 22 is caused by the change in pressure as a result of the blood flow. Alternatively, the movement of the two sections of the membrane 24 back to the closed position can be caused by the two sections being tensioned—by shape memory material or by any known tensioning mechanism.

In accordance with certain alternative implementations, a pivoting valve 10 is provided that is not disposed at 90 degrees in relation to the flow of blood. For example, the valve 10 can be disposed at 60 degrees, 45 degrees, 30 degrees, or any known angle in relation to the blood flow. In some such embodiments, the valve 10 can have an outer circumference that has an elliptical shape, rather than a circular shape.

Figure 6A:
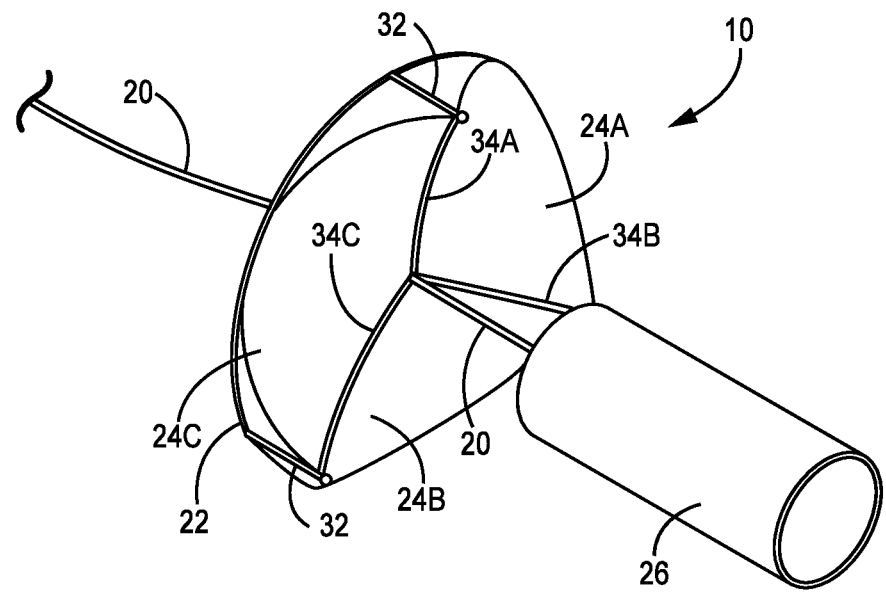
FIG. 6A is a perspective view of a further implementation of a temporary valve.
Figure 6B:
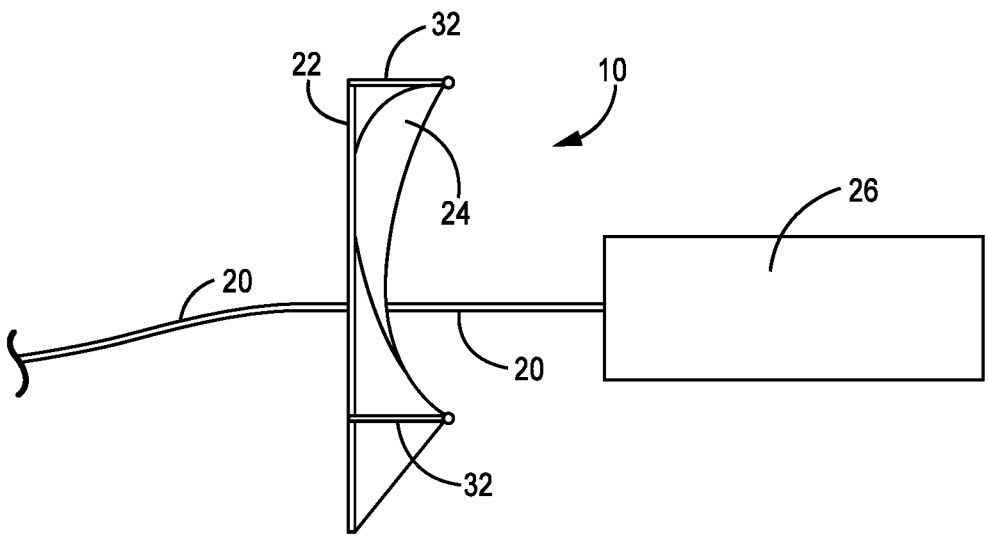
FIG. 6B is the side view of the temporary valve of FIG. 6A.

In FIGS. 6A-6B, an embodiment of the temporary valve 10 which is a tricuspid valve 10 is shown. In this embodiment, the valve membrane 24 is attached to the collapsible frame 22 and to three support pillars 32 that extend in a substantially perpendicularly direction from the collapsible frame 22. This configuration creates three valve leaflets 24A, 24B, 24C that are each attached to the outer collapsible frame 22. Both sides of each leaflet is also attached to the support pillars 32. Thus, the unattached portion of each leaflet 24A, 24B, 24C is the side of the leaflet that is adjacent to the contact seams 34A, 34B, 34C. The leaflets expand away from the guide wire 20 when the pressure increases on one side of the valve membrane 24 to allow blood to flow in the direction of lower pressure. The three leaflets 24A, 24B, 24C then close back together at the contact seams 34A, 34B, 34C between the three leaflets 24A, 24B, 24C when the pressure decreases, thereby creating a seal between each of the leaflets 24A, 24B, 24C and preventing the blood from flowing back in the direction of lower pressure. In this manner, the temporary valve 10 provides the function of controlling blood flow in a desired direction. A tricuspid valve is not the only configuration that is possible with this structure. A bicuspid valve is also possible which would be comprised of just two support pillars 32 with a single seam between two valve leaflets. A valve with four or more leaflets is also possible with a similar support structure for each leaflet.

Figure 7:
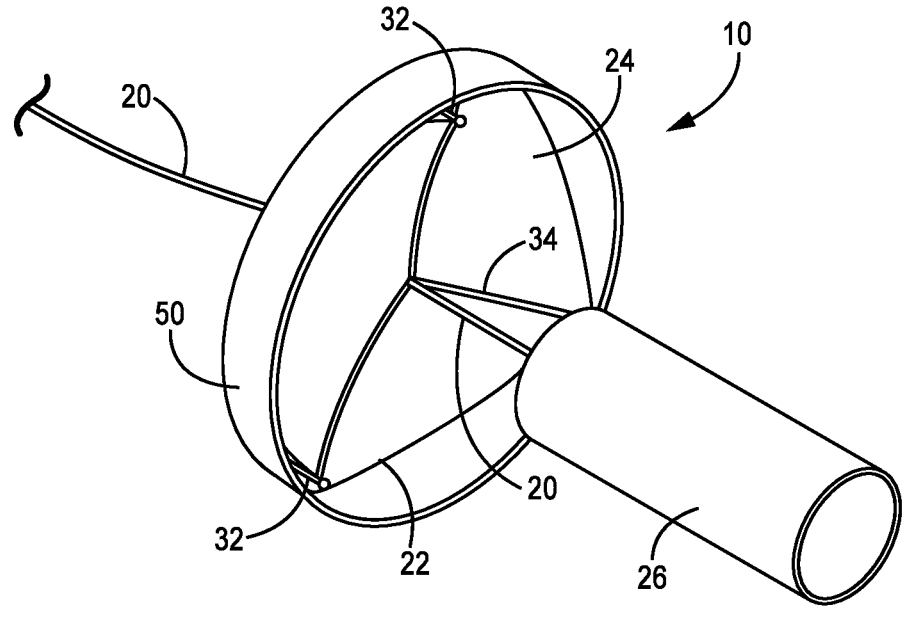
FIG. 7 is a perspective view of another embodiment of a temporary valve.

FIG. 7 depicts a temporary valve 10 that is a tricuspid valve 10 with a compliant skirt 50. In this embodiment, a skirt 50 of compliant material is attached to the outer diameter of the collapsible frame 22 and is disposed external to/outside of the support pillars 32. More specifically, the skirt 50 is disposed around the collapsible frame 22 and support pillars 32 such that the skirt 50 is disposed on or adjacent to a radially external surface of the collapsible frame 22 and the support pillars 32. The compliant material is collapsible for delivery via the delivery sheath 26, and after the collapsible frame 22 expands, the compliant skirt 50 contacts the inner wall of the vasculature to create a seal. In this manner, the compliant skirt 50 helps to facilitate blood flow through the temporary valve 10 as is described herein by preventing blood flow around the outside of the temporary valve 10. The compliant skirt 50 can be made of any manner of material that can collapse and expand and create a seal against the inner wall of the vasculature without damaging the inner wall, such as, but not limited to, polyurethane, polycarbonate, high density polyethylene, and acrylonitrile butadiene styrene, polyester ultrahigh molecular polyethylene, Dacron, and the like. These materials can be uniform sheets, or they can be configured as woven sheets.

Figure 8:
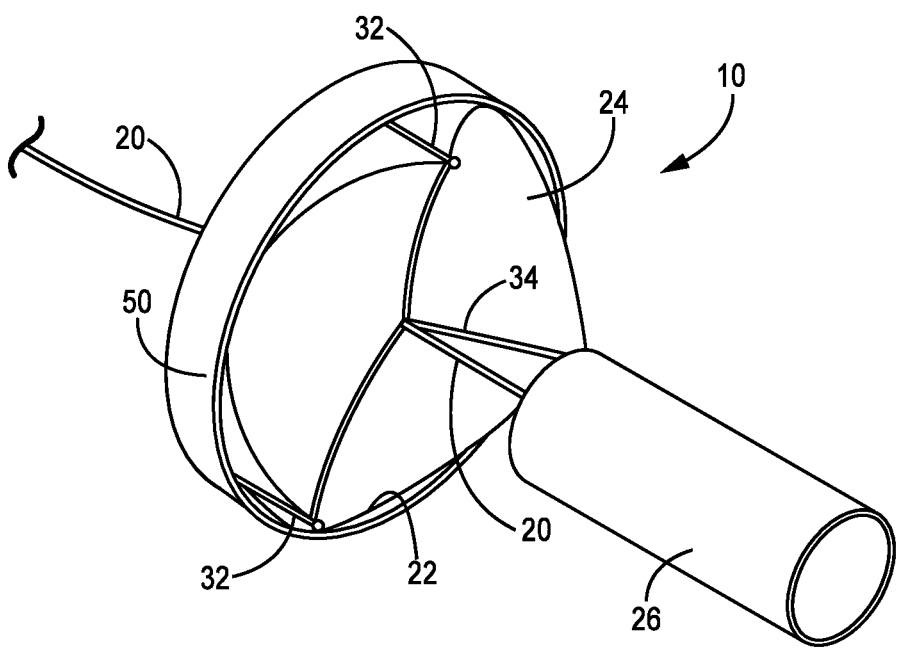
FIG. 8 is a perspective view of a further embodiment of a temporary valve.

A temporary valve 10 that is a tricuspid valve with a compliant skirt 50 is shown in FIG. 8, according to one implementation. In this embodiment, the compliant skirt 50 is attached just to the outer diameter of the collapsible frame 22. The compliant skirt 50 is positioned substantially distal to the collapsible frame 22. In other words, the skirt 50 extends axially from the collapsible frame 22 in the direction opposite that of the support pillars 32. In contrast, in the previous embodiment, the compliant skirt 50 shown in FIG. 7 is attached to the outer diameter of the collapsible frame 22 and outside of the support pillars 32 and is positioned substantially proximal to the collapsible frame 22. That is, in the previous embodiment, the skirt 50 extends axially from the collapsible frame 22 in the same direction as the support pillars 32. The preferred location of the compliant skirt 50 relative to collapsible frame 22 can vary depending on the location of the temporary valve 10 in the patient's vasculature, as different locations will have different adjacent inner vascular anatomy that the compliant skirt 50 seals against.

Figure 9:
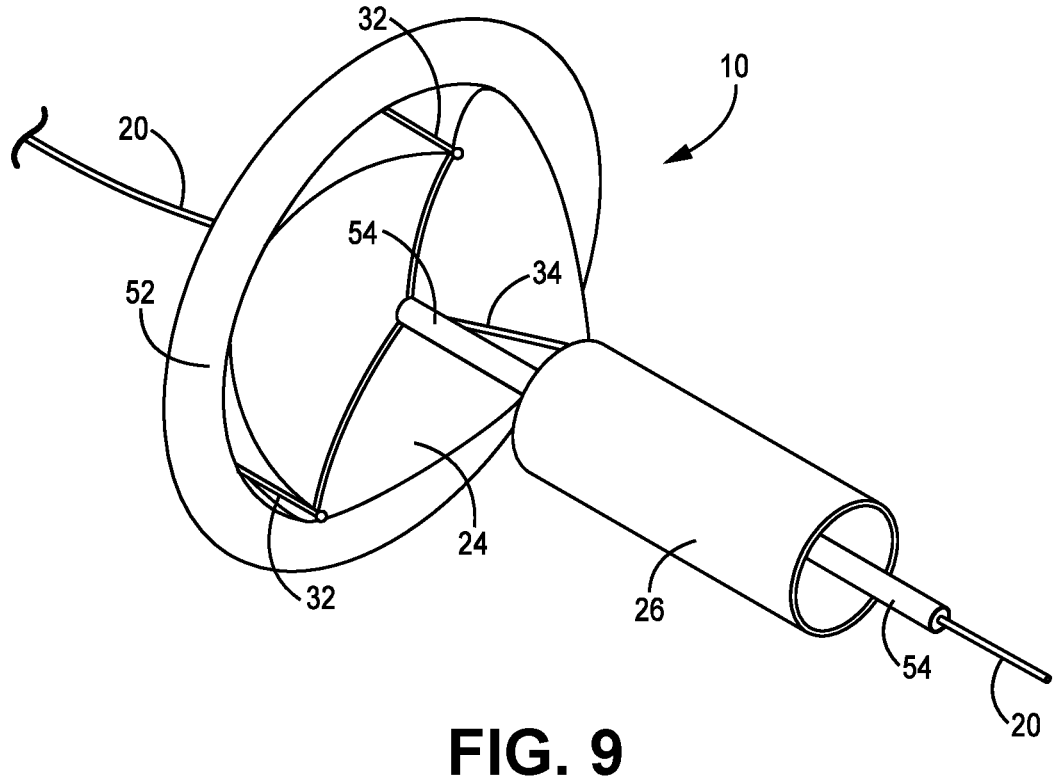
FIG. 9 is a perspective view of yet another embodiment of a temporary valve.

FIG. 9 shows an embodiment of the temporary valve 10 which is a tricuspid valve 10 with an inflatable compliant skirt 52. In this embodiment, an inflatable skirt of compliant material is attached to the outer diameter of the collapsible frame 22 and can also be attached to the radially external outer surface of the support pillars 32. The compliant material is collapsible for delivery via the delivery sheath 26, and after the collapsible frame 22 opens up, the compliant skirt 52 can be inflated with saline or any other known fluid (including any known liquid or gas) for inflation of such a component via a conduit (not shown) such that the compliant skirt 52 contacts the inner wall of the vasculature to create a seal.

In other implementations, the temporary valve embodiments herein can be attached to a delivery sheath or catheter (rather than a guidewire). For example, in FIGS. 10A-10B, an embodiment of a tricuspid temporary valve 10 attached to a delivery sheath 26 is shown. More specifically, in this embodiment, the support struts (not shown) of the valve 10 are attached to a delivery sheath 26 rather than to a guide wire 20 as was the case in the previous embodiments. This temporary tricuspid valve 10 functions in a similar manner to the one described in FIGS. 6A-6B except that the leaflets seal against the contact seams 34 and against the outer diameter of the delivery sheath 26. This temporary valve 10 could also be inserted into the vasculature and advanced to a desired location by collapsing it inside a second delivery sheath (not shown) that is configured coaxially around the outside of the delivery sheath 26 to which the temporary valve 10 is attached such that the valve 10 and delivery sheath 26 can be inserted into and disposed within the second delivery sheath (not shown). This configuration is beneficial in that a temporary valve can provide the desired control of blood flow as is described herein while the delivery sheath 26 provides access for other interventional tools such as, but not limited to, dye delivering catheters, valve retrievers, valve delivery systems, calcification removal tools, tissue removal tools, and the like.

Figure 10A:
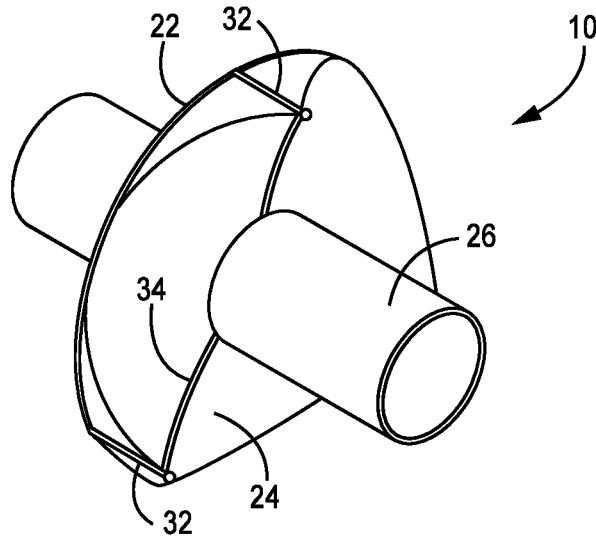
FIG. 10A a perspective view of another implementation of a temporary valve.
Figure 10B:
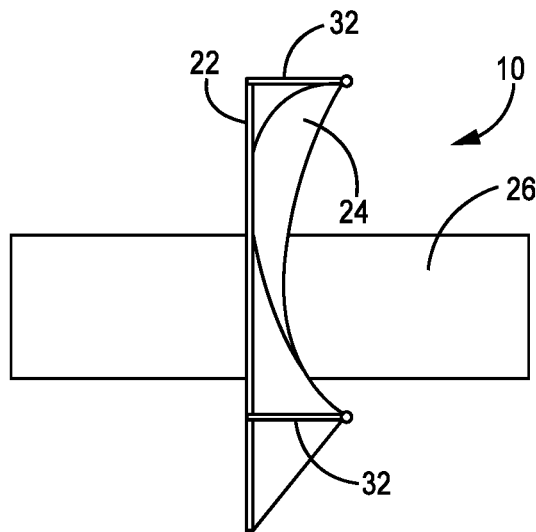
FIG. 10B is the side view of the temporary valve of FIG. 10A.

It is understood that attaching the temporary valve 10 to the outside of a delivery sheath 26 or catheter is not limited to the tricuspid embodiment shown in FIGS. 10A-10B. Any of the previously described embodiments set forth above and depicted in FIGS. 1A-9 that were attached to or delivered over a guide wire 20 could be alternatively attached to a delivery sheath 26 or catheter (instead of a guide wire). The form of the temporary valve 10 is also not limited to the umbrella, flap, pivot, tricuspid, or bicuspid configurations described herein. The temporary valve 10 can take the form of any other type of known valve that can be collapsed in order to be inserted into the vasculature and then expanded once advanced to the desired location such as, but not limited to, duck-bill valves, diaphragm, spiral-shaped valves, etc.

Figure 11A:
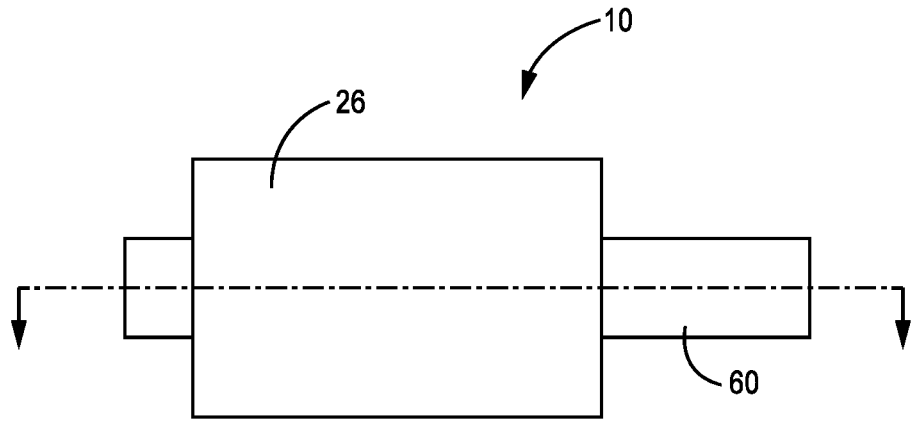
FIG. 11A a side view of a further implementation of a temporary valve.
Figure 11B:
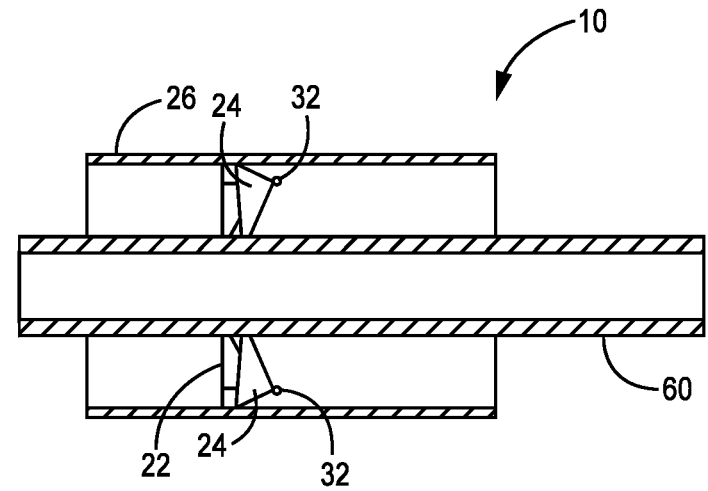
FIG. 11B is the cross-sectional view of the temporary valve of FIG. 11A.

FIGS. 11A-11B depict an embodiment of the temporary valve 10 contained within a delivery sheath 26 and disposed around the outside of a co-axial access sheath 60. In this embodiment, as best shown in the cross-sectional view of FIG. 11B, the temporary valve 10 can be contained inside a delivery sheath 26 in a fully expanded or open configuration. In this manner, the temporary valve 10 can provide the desired control of blood flow through the inside of the delivery sheath 26 as is described herein while the co-axial access sheath 60 provides access for other interventional tools in a fashion similar to that of the device in FIGS. 10A-10B.

Figure 12:
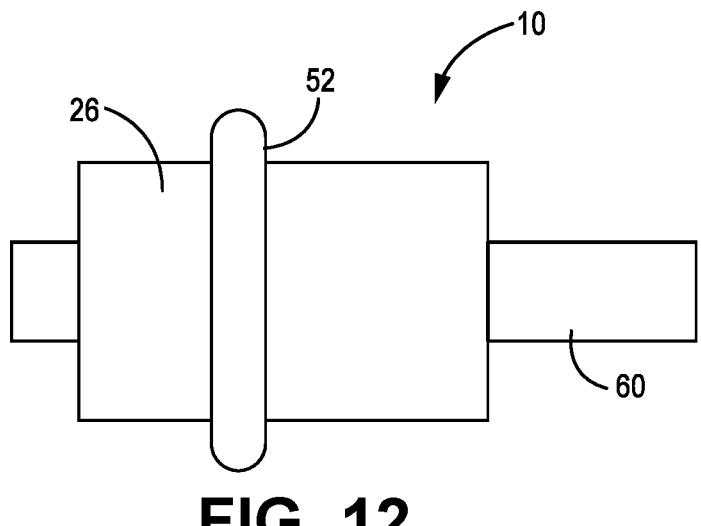
FIG. 12 a side view of yet another implementation of a temporary valve.

Referring to FIG. 12, an embodiment of the temporary valve 10 contained within a delivery sheath 26 and around the outside of a co-axial access sheath 60 is shown with an inflatable compliant skirt 52 is shown. In this embodiment, the inflatable compliant skirt 52 is deflated to a desired location in the vasculature and then can be inflated with saline (or any other known fluid) via a conduit (not shown) such that the compliant skirt 52 contacts the inner wall of the vasculature to create a seal.

The temporary valve 10 embodiments shown in FIGS. 11A-11B and 12 may not be configured with a large enough diameter delivery sheath 26 to allow sufficient blood flow for adequate hemodynamic support through a large vessel in the vasculature such as the aorta, but instead may be configured to temporarily control blood flow in a smaller vessel. The delivery sheath 26 and the enclosed temporary valve 10 need to be of sufficient size to provide adequate blood flow through the blood vessel in which the temporary valve 10 is positioned to support the patient's blood flow need. Further, according to certain implementations, this embodiment may be suitable for venous access where larger diameter delivery sheaths 26 can be accommodated to allow sufficient flow through the device and yet prevent regurgitation flow backwards.

Figure 13A:
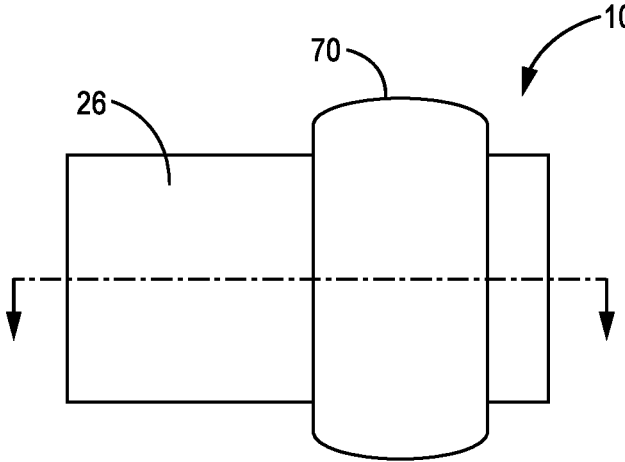
FIG. 13A a side view of another embodiment of a temporary valve.
Figure 13B:
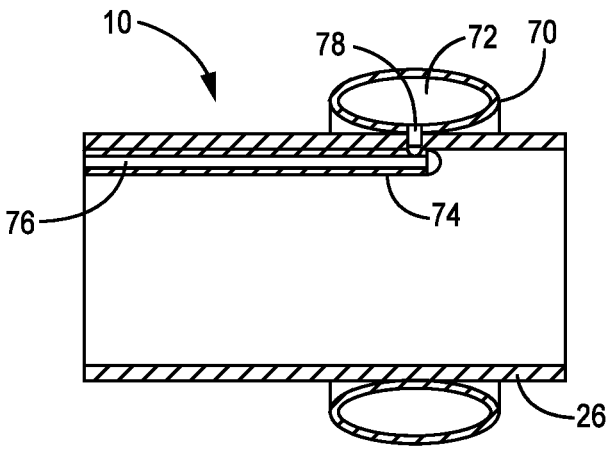
FIG. 13B is the cross-sectional view of the temporary valve of FIG. 13A.

FIGS. 13A-13B depict a temporary valve 10 contained within a delivery sheath 26 with a large inflatable compliant skirt 70, according to one implementation. In this embodiment, an inflatable compliant skirt 70 is disposed around an outer surface of the delivery sheath 26 and is deflated until the temporary valve 10 is position in a desired location in the vasculature and then can be inflated with saline (or any other known fluid for use in such inflation) via a conduit 74 such that the compliant skirt 70 contacts the inner wall of the vasculature to create a seal. As best shown in the cross-sectional view of FIG. 13B, the conduit 74 has an inner lumen 76 and is connected to the inner volume 72 of the inflatable compliant skirt 70 through an opening 78 in the delivery sheath 26. The inflatable compliant skirt 70 can be comprised any manner of material that can collapse and expand and create a seal against the inner wall of the vasculature without damaging the inner wall and that will contain the inflation fluid such as, but not limited to, polyurethane, silicone, latex, polyester, nylon, pebax, PET, and the like. The conduit 74 can be pressurized with saline (or any other known inflation fluid, including, for example, contrast media diluted fluid) via a syringe or syringe pump (not shown) that is outside the body. The conduit 74 can also be in fluid contact with another fluid reservoir (not shown) that is either downstream in the vasculature or outside of the body. The inflatable compliant skirt 70 can act itself as a valve if the inflation fluid in the inner volume 72 is pressurized to a level that prevents blood from flowing back during diastolic pressure but allows blood to flow past (between the inflatable compliant skirt 70 and the inner wall of the vasculature) during higher systolic pressure. The other fluid reservoir can receive the inflation fluid that is pushed out of the inflatable compliant skirt during systolic pressure to allow blood flow past the inflatable compliant skirt, and the other fluid reservoir can return the inflation fluid to the inflatable compliant skirt 70 such that it seals against the inner wall of the vasculature during diastolic pressure. In this manner, a temporary valve 10 that occupies a relatively smaller area around the outside of an delivery sheath 26 or access sheath 60 can provide the hemodynamic function while allowing a relatively large area through the access sheath 60 for performing other functions such as but not limited to the removal of tissue, native valves, TAVR valves, SAVR valves, delivery of new TAVR valve, delivery of contrast, or some other form of therapy.

Figure 14A:
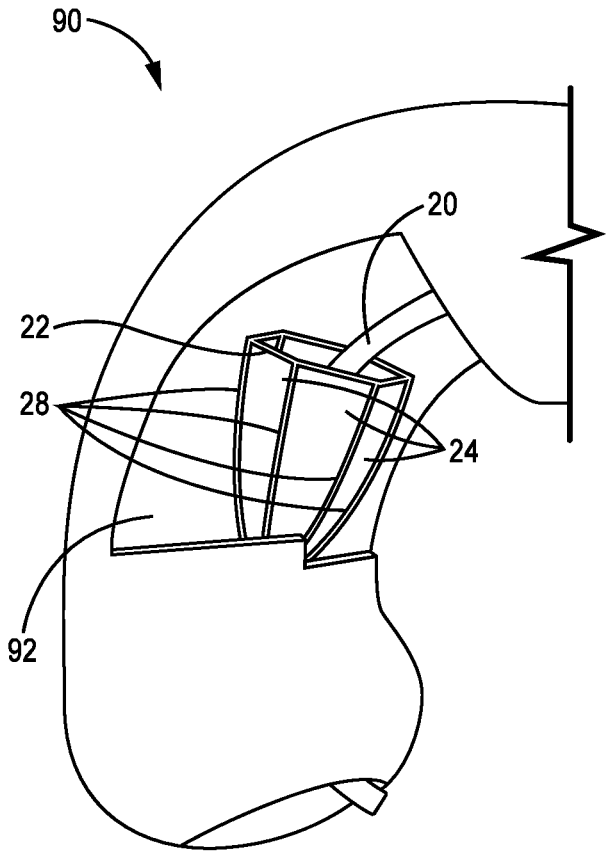
FIG. 14A is a perspective view of another embodiment of a temporary valve positioned within a target vascular area in a collapsed configuration.
Figure 14B:
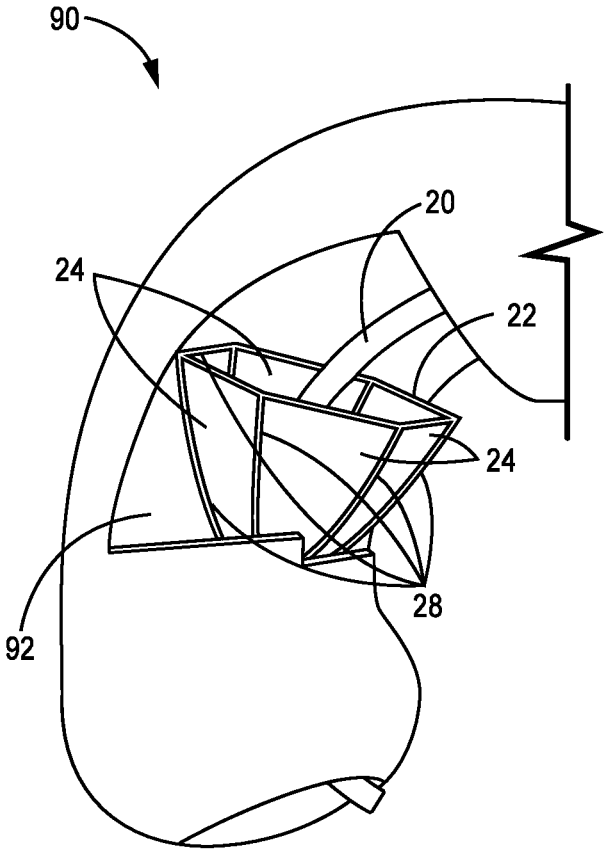
FIG. 14B is a perspective view of the temporary valve of FIG. 14A in an expanded configuration.

FIGS. 14A-14B depict an implementation of a temporary valve 10 that has a substantially conical or umbrella-like shape when in its expanded configuration. As shown in the figures, this exemplary device 10 embodiment is shown positioned at the target vascular area 92 within the vasculature 90. The device 10 is moveable between its collapsed configuration as shown in FIG. 14A and its expanded configuration as shown in FIG. 14B. The device 10 can have an umbrella-like or conical shape and can expand and collapse in a manner similar to the manner an umbrella expands and collapses, by expanding or collapsing the supporting struts 28 away from the guide wire 20 with the valve membrane 24 attached to the supporting struts 28 and frame 22 as shown. More specifically, in this embodiment, the valve membrane 24 is attached to all segments of the collapsible frame 22 and the supporting struts 28 such that there are no openings or gaps therebetween. When the device 10 has been delivered to and positioned in the desired location, the device 10 is then deployed into its expanded configuration as shown in FIG. 14B such that the expandable outer circumference of the frame 22 contacts and establishes a fluidic seal with an inner wall of the target area 92 of the vasculature 90. According to certain implementations, the device 10 is positioned such that the distal end (like the tip of an umbrella) is disposed in the upstream direction (toward the heart) such that the conical configuration allows for blood to flow downstream past the valve 10 but restricts flow upstream. Thus, the conical shape of the temporary valve 10 provides the function of controlling blood flow in a desired direction. Further, when it is time to remove the valve 10, the device 10 can be collapsed by collapsing the supporting struts 28 and frame 22 into a collapsed configuration such that the valve 10 can be retracted. In certain alternative embodiments, the device 10 has no frame 22 at the expandable outer circumference and instead, much like an umbrella, the membrane 24 is attached solely to the expandable supporting struts 28.

In addition, according to certain embodiments, a substantially conical temporary valve 10 such as the exemplary device 10 depicted in FIGS. 14A and 14B can have the added advantage of being able to expand to a size greater than the inner aortic wall (or other inner wall area in the vasculature or heart), thereby creating a seal without requiring an exact fit between the expanded diameter and the inner wall. This cone-shaped temporary valve 10 can be configured to fit a wide range of inner wall diameters with the same sized device, thereby reducing the need for multiple models with different expanded diameters of the temporary valve 10.

It should be noted that any of the various unique features of any embodiment disclosed or contemplated herein can be incorporated into any other implementation. Thus, any version of the compliant skirt as depicted in FIGS. 7-9 and discussed above can be incorporated into any other embodiments herein. Further, any version of the temporary valve device attached to a sheath or catheter as depicted in FIGS. 10A-13B can be incorporated into any other embodiments herein. Similarly, any other features or mechanisms described herein with respect to one embodiment can be incorporated into any of the various embodiments herein.

Although the various embodiments have been described with reference to preferred implementations, persons skilled in the art will recognize that changes may be made in form and detail without departing from the spirit and scope thereof.

What is claimed is:

1. A temporary valve device comprising:
   (a) an expandable frame comprising a flexible material;
   (b) at least one support strut having a first end portion and a second end portion, wherein the first end portion of each support strut of the at least one support strut is attached to the expandable frame, and wherein the second end portion of each support strut of the at least one support strut is positioned radially inward of the expandable frame;
   (c) a membrane attached to the expandable frame; and
   (d) an elongated body that contacts the second end portion of each support strut of the at least one support strut, wherein the elongated body is configured to guide deployment of the expandable frame to a target vascular area, wherein the expandable frame is affixed to the elongated body or configured to be advanced over the elongated body, wherein the elongated body comprises a first portion on a proximal side of the expandable frame and a second portion on a distal side of the expandable frame,
   wherein the temporary valve device is movable into an expanded configuration for deployment of the device in the target vascular area, and
   wherein the temporary valve device is movable into a collapsed configuration for both delivery of the device to the target vascular area and for removal of the device from the target vascular area.

2. The temporary valve device of claim 1, wherein the expandable frame and the membrane have a substantially circular, conical, or umbrella-like shape in the expanded configuration.

3. The temporary valve device of claim 1, wherein the expandable frame and the membrane have a substantially circular shape in the expanded configuration.

4. The temporary valve device of claim 1, wherein a portion of the membrane comprises a flap, wherein at least a portion of the flap is not attached to the expandable frame, wherein the flap is movable between a closed position and an open position in which an opening is defined between the flap and the expandable frame.

5. The temporary valve device of claim 1, wherein the expandable frame is tensioned with an axially outward force when the device is in the collapsed configuration, wherein the axially outward force is sufficient to retain the device within the target vascular area when the frame is expanded to the expanded configuration.

6. The temporary valve device of claim 1, further comprising a flexible skirt attached to an outer circumference of the expandable frame.

7. The temporary valve device of claim 1, wherein the device is positionable within the target vascular area such that the device allows flow of fluid in one direction but inhibits flow of the fluid in an opposite direction.

8. The temporary valve device of claim 1, wherein the temporary valve device in the collapsed configuration is positionable within a lumen of a delivery device.

9. The temporary valve device of claim 8, wherein the delivery device comprises a delivery sheath or a delivery catheter.

10. The temporary valve device of claim 1, wherein the elongated body comprises a guide wire.

11. The temporary valve device of claim 1, wherein the elongated body comprises a catheter or a delivery sheath.

12. The temporary valve device of claim 1, wherein the expandable frame defines an interior, wherein the elongated body extends through the interior of the expandable frame, and wherein the elongated member contacts the at least one support strut at a center point of the expandable frame.

13. A removable valve device comprising:
   (a) an expandable frame;
   (b) at least one support strut attached to the expandable frame;

(c) a flexible membrane attached to the expandable frame and directly attached to and in contact with at least one of the at least one support struts; and (d) an elongated body that is configured to guide deployment of the expandable frame to a target vascular area, wherein the expandable frame is affixed to the elongated body or configured to be advanced over the elongated body, wherein the elongated body comprises a first portion on a proximal side of the expandable frame and a second portion on a distal side of the expandable frame, wherein the removable valve device is movable between a collapsed configuration and an expanded configuration, and wherein the removable valve device is removable in the collapsed configuration after use.

14. The removable valve device of claim 13, wherein the elongated body is a guide wire, wherein each support strut of the at least one support strut has a first end portion attached to the expandable frame and a second end portion directly in contact with the guide wire.

15. The removable valve device of claim 13, wherein the device is positionable within the target vascular area such that the device is configured to allow flow of fluid in one direction but inhibit flow of the fluid in an opposite direction.

16. The temporary valve device of claim 13, wherein the expandable frame defines an interior, wherein the elongated body extends through the interior of the expandable frame, and wherein the elongated member contacts the at least one support strut at a center point of the expandable frame.

17. A method of positioning a temporary valve device within a patient, the method comprising:

inserting the temporary valve device in a collapsed configuration through a blood vessel to a target location in the patient, the temporary valve device comprising:

(a) an expandable frame; and (b) at least one support strut having a first end portion and a second end portion, wherein the first end portion of each support strut of the at least one support strut is attached to the expandable frame, and wherein the second end portion of each support strut of the at least one support strut is positioned radially inward of the expandable frame;

(c) a membrane attached to the expandable frame, wherein inserting the temporary valve device comprises using an elongated body to insert the temporary valve device, wherein the valve body is affixed to the elongated body or configured to be advanced over the elongated body, wherein the elongated body contacts the second end portion of the at least one support strut and comprises a first portion on a proximal side of the expandable frame and a second portion on a distal side of the expandable frame;

expanding the temporary valve device in the blood vessel such that the expandable frame is disposed against an inner wall of the blood vessel, whereby the temporary valve device provides hemodynamic support to the patient; and collapsing the temporary valve device back to the collapsed configuration and retracting the temporary valve device through the blood vessel.

18. The method of claim 17, wherein the retracting the temporary valve device further comprises retracting the temporary valve device through a delivery device disposed in the blood vessel.

19. The method of claim 17, wherein the expanding the temporary valve device comprises releasing the temporary valve device from a delivery device such that an axially outward force resulting from a tensioned state of the temporary valve device in the collapsed configuration causes the temporary valve device to expand to an expanded configuration.

20. The method of claim 17, wherein the collapsing the temporary valve device comprises applying an external force to overcome the axially outward force and thereby urge the temporary valve device into the collapsed configuration.

* * * * *